United States Patent [19]

Pasarela

[11] Patent Number: 4,518,580
[45] Date of Patent: May 21, 1985

[54] EXPANDED CORNCOB GRITS HAVING INCREASED ABSORPTIVITY AND A METHOD FOR THE PREPARATION THEREOF

[75] Inventor: Nunzio R. Pasarela, Brooksville, Fla.

[73] Assignee: American Cyanamid Company, Stamford, Conn.

[21] Appl. No.: 594,946

[22] Filed: Mar. 30, 1984

Related U.S. Application Data

[63] Continuation of Ser. No. 111,563, Jan. 14, 1980, abandoned.

[51] Int. Cl.³ .............................................. A01N 25/26
[52] U.S. Cl. ...................................... 424/16; 424/35; 252/378 R

[58] Field of Search ....................... 252/378 R, 378 P; 424/16, 17; 432/14; 426/445, 447, 449

[56] References Cited

U.S. PATENT DOCUMENTS 2,653,093  9/1953  Baer ..................................... 252/378
3,258,396  6/1966  Schaar ................................... 424/17

Primary Examiner—William R. Dixon, Jr.
Assistant Examiner—Margaret B. Medley
Attorney, Agent, or Firm—H. G. Jackson

[57] ABSTRACT

There are provided novel expanded corncob grits and a method for the preparation thereof. The expanded grits which possess increased absorptivity are found to be useful in the formulation of insecticidal baits, especially fire ant baits, and other agricultural compositions.

2 Claims, No Drawings

EXPANDED CORNCOB GRITS HAVING INCREASED ABSORPTIVITY AND A METHOD FOR THE PREPARATION THEREOF

This application is a continuation of application Ser. No. 111,563, filed Jan. 14, 1980, now abandoned.

The present invention relates to expanded corncob grits and to a method for the preparation thereof. More particularly, the invention relates to expanded grits which possess increased absorptivity, and are found to be useful in the formulation of insecticidal baits, especially fire ant baits, and other agricultural compositions, such as pesticidal formulation, feed additives, and the like. Still more particularly, the present invention relates to insecticidal baits and other agricultural compositions utilizing said expanded corncob grits.

Corncob grits of diverse shape and mesh sizes are known. Usually they are incorporated in a variety of compositions as carriers of biologically active compounds used in the agricultural. Corncob grits, having a bulk density range of from about 384 g/l to about 561 g/l (24 lb/ft$^3$ to 35 lb/ft$^3$) are generally satisfactory for the absorption of liquid formulations, except that their capacity to absorb such liquid formulations is rather limited, and is not more than about 15% by weight of total composition. Higher level compositions appear to be wet and are not free flowing but are sticky.

It has been found by means of the present invention corncob grits are expanded to possess a bulk density range of from about 280 g/l to about 353 g/l (18 to 22 lb/ft$^3$), and which further possess the capacity to absorb increased amounts of liquids to yield compositions containing approximately 20% to about 30% by weight of composition of said liquids, corresponding to approximately 25% to 43% by weight of said grits. The liquids contemplated herein may be a single component or may be formulated from two or more components, for instance, the solution of an insecticide in an edible carrier, such as soybean oil. This product is capable of delivering more active ingredients than the non-expanded starting grit material in a more effective and/or economical manner.

In general, by the process of the present invention, corncob grits are heated at a temperature range of from about 105° C. to about 135° C. at super-atmospheric pressure and in the presence of saturated steam or steam and water in an autoclave for a period of time from about 10 minutes to about 60 minutes. The steam is then rapidly exhausted to the atmosphere; the thus obtained expanded grits are dried if necessary and cooled down to ambient temperature. Although the above method is particularly suitable for use with commercial autoclaves, other devices which are capable of fast heating under pressure and in the presence of saturated steam or steam and water, decompression and drying (as for example an extruder) can also be used.

Thus, for instance, corncob grits of 10/40 mesh size, having a bulk density range of from about 384 g/l to about 561 g/l heated in the presence of saturated steam or steam and water at the temperature range of from about 105° C. to about 130° C. and at a pressure range of from about 1.1 kg cm$^{-2}$ to about 2.8 kg cm$^{-2}$ for a period of time of approximately 10 to 60 minutes. Next the steam is exhausted in the atmosphere, the expanded grits are dried if necessary and cooled to ambient temperature to afford the expanded, highly absorptive corncob grits of the present invention having a bulk density range of from about 280 g/l to about 353 g/l (18 to 22 lb/ft$^3$).

Advantageously, equally good results ca be obtained by heating the corncob grits for a relatively short period of time at or near the maximum temperature range specified above, followed by slow venting of steam to obtain a lower temperature and pressure range, and then holding said grits at that temperature/pressure range for a short period of time, followed by drying and cooling down the thus obtained expanded and highly absorptive corncob grits.

The thus-prepared grits have the capacity to absorb increased amounts of liquids to yield compositions containing approximately 20% to about 30% by weight of composition of said liquids.

As stated above, corncob grits and especially corncob grits that were expanded by the method of the present invention, are well suited for the preparation of baits, when used as carriers of insecticides active as stomach poisons, such as the insecticide of formula (I)

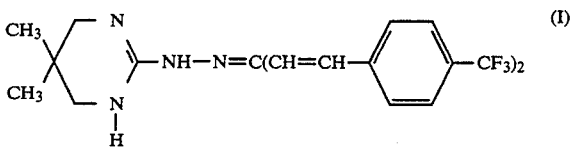

disclosed in U.S. Pat. No. 4,163,102; its method of use disclosed in U.S. Pat. No. 4,087,525 and in application for U.S. patent Ser. No. 004,645, allowed Oct. 19, 1979. The above are incorporated herein by way of reference.

Baits so prepared are effective against insects with chewing mouth parts (Orthopterous insects such as cockroaches, grasshoppers, crickets and Isopterous insects, such as termites). They are effective for the control of fire ants, such as the southern fire ant, *Solenopsis xyloni*, the black imported fire ant, *Solenopsis richteri* and the red imported fire ant, *Solenopsis invicta*. They are also effective for the control of ants, such as the big-headed ant, *Pheidole megacephala*, and the Argentine ant, *Iridomyrmax humilis*, that are dominant pests in pineapple and sugar cane fields, and for the control of many species of ants that are classified under the general category of household ants. Ants are serious economic and public health pests. Serious problems created by fire ants are stinging of humans and livestock, feeding on plants, particularly on seedlings and on germinating seeds, damage to farm machinery that strike ant mounds, loss of crops and refusal of workers to enter infested fields to cultivate and harvest crops. Ants invade houses, crawl over food, carry bits of food to their nests and also cause damage by establishing their nests in the woodwork of houses and other wooden buildings.

Control of these pests can be achieved with treated baits that are distributed in or adjacent to the infested area, such as pasture, park dwellings or other locations in which ant control is desired, and made available to worker ants. The workers carry the treated bait to the colony where it is consumed by the queens and the yound ants, leading to their destruction.

In practice, generally about 1.25 g/ha to 75.0 g/ha, and preferably 2.5 g/ha to 37.5 g/ha of a formula (I) compound is effective for fire ant control and/or for crop protection from ants and about 0.0625% to 4% by weight, and preferably 0.125% to 2.0% by weight of said compound is effective for the control of house ants and/or other insects that are controlled by bait.

Baits can be prepared, for example, by admixing an insecticide with vegetable oils such as soybean oil, and with or without an attractant such as lecitin. The composition is then absorbed on an expanded corncob grits and distributed in the area of the colony or infestation. Use of these baits has particular advantage, since such method of distribution poses little or no hazard to non-target organism that may frequent the infested area.

The invention is further illustrated by the examples set forth below. These examples are provided only by way of illustration and are not intended to be limiting.

EXAMPLE 1

Preparation of expanded corncob grits

Procedure

Corncob grits are autoclaved at 2.10 kg cm$^{-2}$ (29.8 psi; 121° C.) for 30 minutes in the presence of saturated steam. The pressure is then lowered by slow exhaust until the internal temperature drops to 100° C. The autoclave is maintained for an additional 10 minutes at approximately 1.57 kg cm$^{-2}$ (22.4 psi; 112.6° C.), then the pressure is released rapidly and the contents dried for 30 minutes while still in the autoclave.

Three samples are prepared by the above procedure, using corncob grits of 10/40 mesh size and having a bulk density of 466.1 g/l (29.1 lb/ft$^3$).

1. 453 g (1 lb) of grits, as received.
2. 453 g (1 lb) of grits with 1% by weight of water (4.53 g) added, and
3. 453 g (1 lb) of grits, with 5% by weight of water (22.7 g) added.

The samples, after having been expanded by the above procedure have a bulk density range of from 309.2 g/l (19.3 lb/ft$^3$) to 318.6 g/l (19.68 lb/ft$^3$).

The absorptivity of the samples is tested by preparing blends from said grits and soybean oil, containing 20, 25 and 30% by weight of soybean oil, respectively. All blends containing 20 to 25% by weight of soybean oil are free-flowing and dry. Blends containing 30% by weight of oil are somewhat wet and not as free-flowing.

EXAMPLE 2

Preparation of expanded corncob grits

Two samples of corncob grits (about 181 kg each) differing only in particle size distribution are expanded by the method of Example 1, above.

The particle size distribution, bulk density and soybean oil absorptivity of the thus obtained expanded grits is compared to their respective starting materials. The data obtained are summarized in Tables IA and IB below.

TABLE Ia

Summary of particle size distribution and bulk density data

| Sample | Std. Screen | % Distribution before | % Distribution after | Bulk density before | Bulk density after |
|---|---|---|---|---|---|
| A | +20 | 42.8 | 64.7 | 465.5 g/l or 29.06 lb/ft$^3$ | 323.6 g/l or 20.2 lb/ft$^3$ |
|  | +30 | 36.3 | 25.2 |  |  |
|  | +40 | 17.9 | 8.8 |  |  |
|  | −40 | 2.8 | 0.8 |  |  |
| B | +20 | 89.4 | 96.8 | 488.6 g/l or 30.5 lb/ft$^3$ | 410.1 g/l or 25.6 lb/ft$^3$ |
|  | +30 | 10.1 | 3.1 |  |  |
|  | +40 | 0.3 | trace |  |  |
|  | −40 | 0.1 | — |  |  |

TABLE Ib

Summary of Soybean Oil Absorption Data

| Sample | % by wt oil | Appearance of blends prepared from grits before expansion | Appearance of blends prepared from grits after expansion |
|---|---|---|---|
| A | 15 | slightly oily, free flowing |  |
|  | 20 | oily, does not flow | dry, free flowing |
|  | 25 |  | dry, free flowing |
|  | 30 |  | slightly wet |
| B | 15 | very oily, does not flow |  |
|  | 20 | very oily, does not flow | dry, free flowing |
|  | 25 |  | slightly wet |
|  | 30 |  | wet, does not flow |

EXAMPLE 3

Preparation of expanded corncob grits

By the procedure of Example 1 two samples are prepared using corncob grits of 10/40 mesh size and having a bulk density of 464.5±32 g/l (29±2 lbs/ft$^3$).

a One sample is heated for 10 minutes at 2.1 kg cm$^{-2}$ pressure (29.8 psi) and at 121° C. in the presence of saturated steam to yield expanded granules having a bulk density of 323.6 g/l (20.2 lbs/ft$^3$).

b One sample is heated for 10 minutes at 1.35 kg cm$^{-2}$ (19.3 psi) and at 108° C. in the presence of saturated steam to yield expanded granules having a bulk density of 325.2 g/l (20.3 lbs/ft$^3$).

EXAMPLE 4

Evaluation of the effect of variations in the expansion process

By the process of Example 1 above, a number of tests are run using 10/40 mesh corncob grits having a bulk density of 464.5±32 g/l (29±2 lbs/ft$^3$), as follows:

a: A sample is autoclaved for 10 minutes at 2.1 kg cm$^{-2}$ pressure and at 121° C. with saturated steam, the clave is then vented slowly. The pressure is then immediately raised to 2.1 kg cm$^{-2}$ (at 121° C.) and maintained for an additional 10 minutes. The autoclave is then vented rapidly and the sample dried for 15 minutes.

b: As under a except at 1.36 kg cm$^{-2}$ pressure and at 108° C.

c: A sample is autoclaved for 10 minutes at 2.1 kg cm$^{-2}$ pressure and at 121° C. with saturated steam, the clave is then vented rapidly and the sample dried.

d: As under c except at 1.36 kg cm$^{-2}$ pressure and at 108° C.

e: As under c except after venting the clave rapidly, the sample is not dried.

f: As under d except after venting the clave rapidly, the sample is not dried.

Next, the bulk densities, moisture content and oil absorption capacity of the samples are determined. The data thus-obtained are summarized in Table II.

TABLE II

Physical characteristics of samples obtained by the above experiments

| Sample | Bulk density g/l | % Moisture by wt | % oil absorbed; appearance of sample |
|---|---|---|---|
| A | 318.8 | 7.9 | 20; v. slightly oily, |

TABLE II-continued

Physical characteristics of samples obtained by the above experiments

| Sample | Bulk density g/l | % Moisture by wt | % oil absorbed; appearance of sample |
|---|---|---|---|
| B | 336.4 | 7.3 | free flowing* 25; slightly oily, free flowing 20; v. slightly oily, free flowing* 25; slightly oily, free flowing |
| C | 323.6 | 6.1 | 20; v. slightly oily, free flowing* 25; slightly oily, free flowing |
| D | 325.2 | 3.6 | 20; v. slightly oily, free flowing* 25; slightly oily, free flowing |
| E | 307.6 | 7.1 | 20; v. slightly oily, free flowing* 25; slightly oily, free flowing |
| F | 315.6 | 7.7 | 20; v. slightly oily, free flowing* 25; slighty oily, free flowing |

*v = very

We claim:

1. Expanded corncob grits characterized as having a bulk density range of from 280 g/l to 353 g/l and absorbed therein insecticidal containing liquids of from 25% to 43% by weight of the grits.

2. The product according to claim 1, wherein the liquid is soybean oil having dissolved therein 1.25% to 2.5%, by weight, tetrahydro-5,5-dimethyl-2-(1H)-pyrimidinone-{3-[4-trifluoromethyl)phenyl]-1-{2-[4-trifluoromethyl)phenyl]ethenyl}-2-propenylidene}hydrazone, based on the weight of the oil.

* * * * *